United States Patent
Singh et al.

(10) Patent No.: US 6,869,784 B2
(45) Date of Patent: Mar. 22, 2005

(54) PASSIVATION OF NERVE AGENTS BY SURFACE MODIFIED ENZYMES STABILIZED BY NON-COVALENT IMMOBILIZATION ON ROBUST, STABLE PARTICLES

(75) Inventors: Alok Singh, Springfield, VA (US); Mehran Pazirandeh, Silver Spring, MD (US); Paul E. Schoen, Alexandria, VA (US); Michael A. Markowitz, Burke, VA (US); J. Matthew Mauro, Silver Spring, MD (US)

(73) Assignee: The United States of America as represented by the Secretary of America, Washington, DC (US)

( * ) Notice: Subject to any disclaimer, the term of this patent is extended or adjusted under 35 U.S.C. 154(b) by 0 days.

(21) Appl. No.: 09/725,309

(22) Filed: Nov. 29, 2000

(65) Prior Publication Data

US 2004/0029243 A1 Feb. 12, 2004

(51) Int. Cl.$^7$ .................................................. C12N 9/96
(52) U.S. Cl. ........................ 435/188; 435/180; 435/181; 435/440; 435/176; 435/177; 435/178; 435/6
(58) Field of Search ............................. 435/180, 183, 435/440, 176, 177, 178, 6

(56) References Cited

U.S. PATENT DOCUMENTS

| | | |
|---|---|---|
| 4,264,766 A | 4/1981 | Fischer |
| 4,266,029 A | 5/1981 | Branner-Jørgensen ...... 435/176 |
| 4,420,559 A | 12/1983 | Zimmermann ............... 435/99 |
| 4,462,832 A | 7/1984 | Jettmar et al. ............... 100/23 |
| 4,589,881 A | 5/1986 | Pierschbacher et al. .. 623/23.76 |
| 4,748,121 A | 5/1988 | Beaver et al. ............... 431/176 |
| 4,781,951 A | 11/1988 | Kitamura et al. ............. 428/17 |
| 4,808,530 A | 2/1989 | Means et al. ............... 435/180 |
| 4,859,594 A | 8/1989 | Portier .................... 435/172.1 |
| 4,931,498 A | 6/1990 | Pidgeon ..................... 525/54.1 |
| 5,080,898 A | 1/1992 | Murphy ..................... 429/94.1 |
| 5,366,881 A | 11/1994 | Singh et al. ................ 435/177 |
| 5,397,755 A | 3/1995 | Parker et al. .................. 502/7 |
| 5,571,705 A | 11/1996 | Pierce ........................ 435/174 |
| 5,663,387 A | 9/1997 | Singh .......................... 554/80 |
| 5,695,750 A | 12/1997 | Doctor et al. .............. 429/94.1 |
| 5,760,089 A | 6/1998 | Cronce ....................... 514/643 |
| 5,859,064 A | 1/1999 | Cronce ....................... 514/643 |
| 5,928,927 A | 7/1999 | Cheng et al. ............... 435/196 |
| 6,593,099 B2 * | 7/2003 | Xiao et al. .................... 435/19 |

OTHER PUBLICATIONS

Lee et al., C–terminal His–Tagging Results in Substrate Specificity Changes of the Thioesterase I from *Escherichia coli*, Journa of the American Oil Chemist's Society, vol. 76, No. 10, pp 1113–1118, 1999.*

Carlsson et al., Affinity Precipitation and Site–Specific Immobilization of Proteins Carrying Polyhistidine Tails, Biotechnology an Bioengineering, vol. 51, pp. 221–228, 1996.*

Qiagen Product Guide, 1997, pp. 106–110.*

Lu et al., Histidine Patch Thioredoxins, Journal of Biological Chemistry, Mar. 1996, vol. 271, No. 9, pp. 5059–5065.*

LeJeune et al., Dramatically Stabilized Phosphotriesterase– Polymers for Nerve Agent Degradation, Biotechnology and Bioengineering, Apr. 1997, vol. 54, No. 2, pp. 105–114.*

Polayes et al., Efficient Protein Expression and Simple Purification Using the pProEX–1™ System, Life Technologies–FOCUS, Jul. 1994, vol. 16, p. 81–84.*

* cited by examiner

*Primary Examiner*—Richard Hutson
(74) *Attorney, Agent, or Firm*—John J. Karasek; Joseph T. Grunkemeyer; Amy Ressing

(57) ABSTRACT

Enzymes are modified by incorporating anchor sites for linking the enzymes to a target surface without destroying the catalytic activity of the enzymes. A stable carrier to accommodate and bind the selected enzyme is constructed, and the enzyme is non-covalently linked to the carrier, generally through metal salts of iminodiacetate.

8 Claims, No Drawings

PASSIVATION OF NERVE AGENTS BY SURFACE MODIFIED ENZYMES STABILIZED BY NON-COVALENT IMMOBILIZATION ON ROBUST, STABLE PARTICLES

FIELD OF THE INVENTION

The present invention relates to a detoxification/decontamination system for nerve agents which has long term stability over a wide temperature range.

BACKGROUND OF THE INVENTION

Nerve agents pose a growing threat to society whether they are released accidentally or deliberately. Current means to counter threats from nerve agents, although temporarily effective, are not adequate. Currently, activated charcoal is used to filter nerve agents from air and water; bleach solution or jet fuel is used for decontaminating protective gear. However, these methods use compositions which have undesirable properties including corrosiveness, flammability, and toxicity. Moreover, these methods can only be used on a small scale, and they are not effective over an extended period of time.

Delivery of active enzyme systems to counter and detoxify chemical and biological warfare agents is a promising and active area of research. While some enzymes in their native form have exhibited effectiveness against nerve agents, there are still many challenges in developing effective detoxification systems, including preservation of high catalytic activity in real conditions, stability of the enzyme system after prolonged storage, suitable means of delivery, and accessability of enzymes to threat agents.

"Detoxifying Nerve Agents", C&E News Sep. 15, 1997, page 26 reports the current state of the art for detoxification of nerve agents, with special reference to efforts on the part of the U.S. Army. A class of enzymes that is known to catalyze the hydrolysis of organophosphate compounds has been investigated for potential decontamination. The organophosphate anhydrolases (OPAA: EC3.1.8.2) catalyze the hydrolysis of many G-type chemical warfare nerve agents. Specifically, these enzymes have activity against compounds such as sarin, soman, and GF (O-cyclohexyl methylphosphono fluoridate). Covalently linking enzymes to solid substrates and embedding enzymes in polymer matrices are the two most common means for enzyme immobilization. However, the covalent chemistry required for linking an enzyme to a substrate often adversely affects the enzyme's activity. Enzymes embedded in polymer matrices are not accessible freely to the agents present in the surrounding medium.

Branner-Jorgensen, in U.S. Pat. No. 4,266,029, disclose immobilizing enzymes on a mineral oxide which has been coated with gelatin and glutaraldehyde. However, these enzymes are used in fluidized bed operations, and there is no indication that these enzymes can be used to detoxify nerve agents.

Doctor et al., in U.S. Pat. No. 5,366,881, disclose mutant cholinesterase which can be used for detoxifying organophosphates. However, to maintain the activity of the cholinesterases, oximes are added.

Tschang et al., in U.S. Pat. No. 4,461,832, disclose enzymes embedded in silica gel in order to suspend the enzyme. There is no indication that these enzymes retain their activity, or that these enzymes can be used to detoxify nerve agents.

Recently, LeJeune and coworkers reported immobilizing phosphotriesterases onto polyurethane polymers for decontamination purposes (LeJeune et al., Biotechnology and Bioengineering 54:105–114, 1997. However, there are several drawbacks to using polyurethane for immobilizing phosphotriesterases. In addition to being an environmentally unfriendly polymer, polyurethane may not afford the maximal protein stability that can be achieved in the protein's native environment. In addition, the enzymes used in these studies have not been selected for use under field conditions, and suffer many drawbacks, including inhibition by substrate, low turnover, and low stability. Watkins et al., Biological Chemistry 272:25596–25601, 1997) have demonstrated enhanced rate of hydrolysis of phosphorus-fluorine bonds by phosphotriesterases using engineered enzymes.

SUMMARY OF THE INVENTION

It is an object of the present invention to overcome the deficiencies of the aforementioned prior art.

It is another object of the present invention to provide a mutagenesis and selection/screening method to obtain enzymes with the desired catalytic and stability properties.

It is a further object of the present invention to modify the enzymes obtained for non-covalent immobilization on the surface of polymerized vesicles.

It is another object of the present invention to modify the enzymes obtained for non-covalent immobilization on the surface of silica particles.

The following method is used to produce effective agents for detoxifying/decommissioning nerve agents:

(1) Select a suitable enzyme.

(2) Modify the enzyme by incorporating anchor sites for linking it to a target surface without destroying the catalytic activity of the enzyme.

(3) Construct a stable carrier to accommodate and bind the selected enzyme.

(4) Non-covalently link the enzyme to the colloids of surface metal iminodiacetate groups and/or nitrilotriacetic acid groups.

Once an enzyme has been selected for its catalytic and stability properties, the enzyme is further modified for non-covalent immobilization on the surface of polymerized vesicles. The immobilization technique is the subject of U.S. Pat. No. 5,663,387, the entire contents of which are hereby incorporated by reference. Polymerized liposomes are a prime substrate for immobilizing active enzymes because they retain their structural integrity in adverse chemical and physical environments, provide a native environment for enzymes to sustain their activity, and provide higher surface area to facilitate easy access of medium to enzymes.

Silica particles can also be used as substrates for non-covalent enzyme immobilization, because these particles have high surface area and retain their structural integrity in adverse chemical and physical environments. Silica particles with surface IDA groups can be formed in at least one of two ways:

(1) Silica particle precursors, such as TEOS or TMOS are to be co-hydrolyzed with IDA-modified alkoxysilanes using the Stober process (Stober et al., Journal of Colloid Interface Science 26:62, 1968); or (2) IDA alkoxysilanes are grafted to the surface of silica particles using well established procedures, Bradley et al., Langmuir 6: 792, 1990; Van Blaaderen et al., Langmuir 8:2921, 1992). After forming a metal IDA salt or a metal NTA salt, non-covalent enzyme immobilization can proceed as previously described. Since enzymes immobilized onto silica or other inorganic particles can be packed into a variety of chromatographic columns (liquid HPLC), they readily lend themselves to simultaneous continuous-flow catalytic processing of multiple toxic agents. This appears to be the first time that surface modified enzymes have been immobilized on silica particles.

DETAILED DESCRIPTION OF THE INVENTION

According to the present invention, using either a liposome or silica particle, customized immobilization protocols can be developed and optimized for storing the enzyme systems under otherwise adverse conditions.

Examples of enzymes which are useful in detoxifying nerve agents arc thioesterases, although the process of the present invention can be used with any type of enzyme useful for destroying waste materials. One example of this is lipase, which is used for digesting waste onboard ships. The enzymes are genetically engineered to include a poly-His tail as well as other stabilizing amino acid substitutions. Non-covalent enzyme immobilization on polymerized liposomes was effected by co-polymerizing amphiphiles containing metal salts of iminodiacetic acid or nitrilotriacetic acid with other polymerizable amphiphiles and then binding the enzyme to the iminodiacetic acid-metals or NTA-metal salts on the outer surfaces of the vesicles. This technique relics on the strong binding affinity between iminodiacetate salts or NTA salts and polyhistidine, which has been made available on the surface of the enzyme selected for immobilization through genetic engineering. The enzymes that can be used for this technique are those enzymes that have appropriately reactive surface available histidines or which have a histidine tag that can be added through site specific mutagenesis. This includes, or course, polyhistidine. Histidine forms a strong bond with iminodiacetic acid salts, such as copper, zinc, cobalt, and nickel iminodiacetate salts, and nitrilotriacetic acid salts, such as copper, zinc, cobalt, and nickel salts. The main criterion for this process to be effective is that the binding site on the enzyme be far away from or innocuous to the function of the enzyme's catalytic site. While silica is the preferred inorganic surface because it is relatively inexpensive and its properties are well understood, any typo of metal oxide ceramic particles that can be formed similar to the Stober process starting with a metal alkoxide precursor can be used. Other types of inorganic surfaces that can be used in the process of the present invention include alumina, baria. titania, and zirconia.

Bachmair et al., in U.S. Pat. Nos. 5,646,017; 5,496,721; 5,196,321; 5,132,213; and 5,093,242, the entire contents of which are hereby incorporated by reference, disclose methods for designing or modifying protein structure at the protein or genetic level to produce proteins having specified amino-termini in vivo or in vitro. These methods can be used to produce proteins having amino-termini on enzymes wherein gene encoding the enzymes can be made to encode an amino acid of the desired class at the amino-terminus so that the expressed enzyme exhibits a predetermined amino-terminal structure which renders it metabolically stable and able to bind to metal salts of iminodiacetic acid which are copolymerized with amphiphiles. Preferably, the amino-terminal structure is histidine, although C-terminal or internal poly-His sequences will usually be satisfactory as well.

A DNA sequence containing nucleotides coding for the enzyme of interest, as well as nucleotides which code for an amino acid sequence at the N-terminus or C-terminus of the enzyme such as histidine which strongly bind to metal iminodiacetate or nitrilotriacetic acid salts are operably linked to a promoter that will permit expression of the enzyme in the cells of interest for production thereon. This enzyme cassette is introduced into cells for production of the stabilized enzyme, after which the stabilized enzymes are recovered therefrom by conventional means.

The enzymes useful in detoxifying nerve agents are attached to iminodiacetate salt groups on the surface of silica particles formed by co-hydrolyzing TMOS with an IDA-alkoxysilane derivative. The IDA-alkoxysilane derivative accounted for 5 weight percent of the total silica content. After particles were synthesized using the Stober procedure, the copper salt of the surface IDA groups was formed by adding an aliquot of 20% aqueous $CuSO_4$ solution (wt/wt) to the dry particles, and then suspending the particles using mild sonication or vortex mixing. The suspension was centrifuged and the supernatant was removed. This procedure was repeated, and the resulting blue silica particles were washed with water by adding the water to the particles, suspending the particles in solution, and then centrifuging the suspension and removing the supernatant. This procedure was repeated three times. Then, an aliquot of the thioesterase in 0.05 M phosphate buffer, pH 7.2, was added to a suspension of the particles in the same buffer. The suspension was incubated at 4° C. for three hours. The particles were then centrifuged and the supernatant was removed. The particles were then washed using the phosphate buffer described above. All operations involving the enzyme were performed at 4° C. After the final washing, the particles were resuspended in the buffer and stored for future use. The activity of the immobilized enzyme was confirmed using standard procedures.

EXAMPLES

1. Cloning and Modifying Enzyme

The gene for thioesterase-1 (TE-1) of *E. coli* strain JM109 was cloned using a modification of the procedure published in *Escherichia coli:* thioesterase I. Molecular cloning and sequencing the structural gene and identification of a periplastic enzyme, Hyeson Cho, John L. Carona (1993) Journal of *Biological Chemistry* 268: 9238–9245. Briefly, amplified DNA encoding the TE-1 protein and appropriate flanking nucleotide sequences was ligated into the DNA vector PCR 2.1 (Invitrogen). After preparing of 140 micrograms of the PCR2.1-TE1 vector DNA from 100 ml overnight culture, the engineered TE-1 fragment was liberated from the intermediate vector by digestion of 10 micrograms of this DNA with 20 units each of the restriction endonucleases NdeI and XhoI at 37° C. overnight. The liberated TE-1 coding fragment was purified electrophoretically on a 2% agarose gel. The stained gene fragment was excised from the gel and subsequently obtained free of agarose using commercial products (Qiagen).

The gene for N-terminal polyhistidine-modified TE-1 was prepared by enzymatically ligating approximately 300 μg of the gene fragment described above with about 100 ng of pProEx-1 vector DNA (Life Technologies) previously digested with NdeI and XhoI enzymes and dephosphorylated with calf intestinal alkaline phosphatase. Transformed *E. coli* DH5αF'LacI$^q$ cells (Life Technologies) were screened for the presence of the TE-1 inserted gene by electrophoretic analysis of differential whole-cell protein profiles of cells taken from small scale cultures grown plus and minus 1 mM isopropylthiogalactopyranoside (1PTG) chemical inducer.

TE-1 was purified from 100 ml cell culture (LB/50 micrograms/ml carbenicillin) induced at 30° C. with 1 mM for about two hours ($OD_{600}$ at induction ~0.6). Cell resuspension, sonic lysis, and chromatographic purification were carried out according to published procedures published in Protein Biotechnology (1993) Felix Franks, Human Press, Totwa, N.J., and references cited therein. The final eluted TE-1 product, 14 ml, was dialyzed for three days against 3 L 50 mM potassium phosphate buffer, pH 7.2. The dialyzed product was concentrated in two stages to 0.65 ml using Centriprep-10 and Centricon-10 centrifugal concentrators at 4° C. The final protein concentration of 0.35 mg/ml was evaluated against bovine serum albumin standard protein using a Bio-Rad (Bradford method) assay kit.

2. Assay of Enzymatic Activity Immobilized TE-1

Samples of TE-1 immobilized on IDA silica were assayed for their ability to hydrolyze p-nitrophenyl propionate (SIGMA) according to published procedures. In a typical assay, equivalent amounts of silica/enzyme slurry, or appropriate control samples, in 10 to 20 microliters were added to a 1.5 ml polypropylene conical microcentrifuge tube that contained 0.97 ml physiologically buffered saline (PBS) at pH 7.2, 3% v/v acetone, and 0.370 mM p-nitrophenyl propionate. Each tube was capped, oriented on its side, and shaken at 225 RPM at 30 C. for 30 minutes. After 30 minutes, each sample was immediately centrifuged at room temperature for exactly one minute. Then, 0.90 ml of each sample was removed and immediately assayed spectrophotometrically at 346 nm. In one such assay, the background corrected results were as follows:

| Sample | Activity ($OD_{346}$units/min × $10^3$) |
|---|---|
| $Cu^{2+}$ + IDA silica + TE-1 | 5.12 |
| $Cu^{2+}$ + IDA silica | 0.47 |
| IDA silica | 0.67 |

3. Formulation and Catalytic Activity of $Cu^{2+}$-IDA Silica Particles

The silica particles were formed by co-hydrolyzing TMOS with an IDA-alkoxysilane. The IDA-alkoxysilane accounted for 5 weight % of the total silica content. After particle synthesis using the Stober procedure, the copper salt of the surface IDA groups was formed by adding an aliquot of aqueous 20% $CUSO_4$ solution, w/w, to the dry particles, and then suspending the particles using mild sonication and vortex mixing. The suspension was centrifuged and the supernatant was removed. This procedure was repeated, and then the resulting blue silica particles were washed with water by adding the water to the particles, suspending the particles in solution, and then centrifuging the suspensions and removing the supernatant. This procedure was repeated three times. A small portion of these particles was further washed with an aqueous saturated EDTA tetrasodium salt solution in a similar manner. Upon adding the EDTA solution, the supernatant turned from clear to blue and the particles turned from blue to white, demonstrating that copper ions had been bound to the IDA groups on the surface of the particles.

Then, the $Cu^{2+}$-IDA particles were suspended by mild sonication and vortex mixing in 1 ml of 0.005 M aqueous phosphate buffer, pH 7.2. Then, 40 μL of this suspension was added to a test tube. 160 μL of the buffer was added, and the resulting suspension was cooled to 4° C. After three hours at 4° C., the catalytic activity of the particles was tested using a thioesterase assay. The particles exhibited catalytic activity as follows:

$Cu^{2+}$+IDA silica particles, 0.47 $OD_{346}$ units/mm×$10^3$
IDA silica particles, 0.67 $OD_{346}$ units/min×$10^3$ This example demonstrates that the $Cu^{2+}$+IDA particles have no catalytic activity in the absence of bound thioesterase.

4. Binding and catalytic Activity of Thioesterase on $Cu^{2+}$-IDA Silica Particles Polyhistidine tagged thioesterase was noncovalently attached to copper-IDA groups on the surface of silica particles made as in Example 1 in the following manner: 40 μL of the suspension of the $Cu^{2+}$+IDA silica particles in 1 ml of 0.05M aqueous phosphate buffer, pH 7.2., suspension was added to a test tube. 160 μL of the buffer was added, and the resulting suspension was cooled to 4° C. Then, 10 μL of the thioesterase in the phosphate buffer was added to this suspension, which was then incubated at 4° C. for three hours. The particles were centrifuged and the supernatant was removed, making sure that the silica did not go dry. The particles were washed using the phosphate buffer as described above. Eight mL of the buffer was added to the particles, which were then suspended with mild sonication, centrifuged, and the supernatant removed. This washing procedure was repeated six times. All operations involving the enzyme were performed at 4° C. After the final washing, the particles were resuspended in 1 mL of the buffer and stored for future use. The activity of the immobilized enzyme was confirmed using standard procedures. This sample, $Cu^{2+}$+IDA silica+TE-1 showed an activity of 5.12 $OD_{346}$ units/min×$10^3$. This example demonstrates the sustained activity of polyhistidine modified thioesterase bound to the $Cu^{2+}$-IDA groups on the silica particles.

5. Binding and Catalytic Activity of Thioesterase on IDA with Silica Particles

The $Cu^{2+}$-IDA silica particles that had been washed with saturated aqueous tetrasodium EDTA solution were resuspended in 1 mL of 0.05 M aqueous phosphate buffer at pH 7.2. 40 μL of the suspension of this suspension was added to a test tube. 160 μL of the phosphate buffer was added, and the resulting suspension was cooled to 4° C. Then, 10 μL of thioesterase in phosphate buffer was added to this suspension, which was then incubated at 4° C. for three hours. The particles were centrifuged and the supernatant was removed, making sure that the silica did not go dry. The particles were washed using the phosphate buffer as described above. Eight mL of the buffer was added to the particles, which were then suspended with mild sonication, centrifuged, and the supernatant removed. This washing procedure was repeated six times. All operations involving the enzyme were performed at 4° C. After the final washing, the particles were resuspended in 1 mL of the buffer and stored for future use. The catalytic activity of these particles, as determined by the thioesterase assay, was significantly less than the activity of the enzyme bound to the $Cu^{2+}$-IDA particles. This example demonstrates that binding of the enzyme to the $Cu^{2+}$-IDA groups on the silica particles is required for optimal catalytic activity.

The method of the present invention provides means for stabilizing enzymes in such a fashion that the enzymes, by virtue of their non-covalent bonding to the liposomes or silica, are readily available to act on their substrates. The present invention provides an effective system that uses the efficiency and selectivity of enzymes in catalysis and utility of surfaces to provide stability to sophisticated enzyme architecture.

The foregoing description of the specific embodiments will so fully reveal the general nature of the invention that others can, by applying current knowledge, readily modify and/or adapt for various applications such specific embodiments without departing from the generic concept, and, therefore, such adaptions and modifications should and are intended to be comprehended within the meaning and range of equivalents of the disclosed embodiments. It is to be understood that the phraseology or terminology employed herein is for the purpose of description and not of limitation.

What is claimed is:

1. A method for stabilizing a thioesterase comprising:
    genetically engineering the thioesterase to include one or more terminal histidine residues;
    copolymerizing an amphiphile containing a salt selected from the group consisting of metal salts of iminodiacetic acid, nitrilotriacetic acid, and mixtures thereof with other polymerizable amphiphiles to form vesicles; and
    binding the genetically engineered thioesterase to the salts on the outer surface of the vesicles.

2. The method according to claim 1 wherein the metal salts are selected from the group consisting of copper, nickel, cobalt, and zinc salts.

3. The method according to claim 1 wherein the salt is a metal salt of iminodiacetic acid.

4. The method according to claim 1 wherein the salt is a metal salt of nitrilotriacetic acid.

5. The method of claim 1 wherein the bound enzyme is capable of detoxifying a nerve agent.

6. The method of claim 1 wherein the enzyme includes a terminal polyhistidine chain.

7. The method of claim 1 wherein the bound genetically engineering thioesterase is catalytically active.

8. The method of claim 1, further comprising the step of contacting the bound thioesterase with a sample suspected of containing a contaminant.

* * * * *